United States Patent [19]

Bailey, Jr.

[11] 4,214,585
[45] Jul. 29, 1980

[54] TOOL FOR SURGICAL IMPLANTATION OF AN INTRAOCULAR LENS

[76] Inventor: Paul F. Bailey, Jr., 4885 NW. Barnes Rd., Portland, Oreg. 97210

[21] Appl. No.: 905,574

[22] Filed: May 15, 1978

[51] Int. Cl.² .................. A61F 9/00; A61F 1/16; A61F 1/24
[52] U.S. Cl. .................................. 128/303 R; 3/13
[58] Field of Search ........................ 3/13; 128/303 R

[56] References Cited
U.S. PATENT DOCUMENTS

| 3,996,626 | 12/1976 | Richards | 3/13 |
| 4,085,467 | 4/1978 | Rainin et al. | 3/13 |
| 4,124,905 | 11/1978 | Clark | 3/13 |
| 4,136,406 | 1/1979 | Norris | 3/13 |

Primary Examiner—Ronald L. Frinks
Attorney, Agent, or Firm—Kolisch, Hartwell & Dickinson

[57] ABSTRACT

An intraocular lens for surgical implantation in the eye includes a lens body, posterior loops extending from the lens body for orienting the lens body in the eye's anterior chamber and a novel clip joined to the lens body. The clip extends into an iridectomy provided in the iris, when the lens body is implanted, in a nonstressed condition to thereby attach the iris to the lens body, flexing of the clip being required prior to its being extended into the iris. A surgical tool having an elongated means with a longitudinal bore therethrough slideably receives the clip in a flexed stressed condition while simultaneously holding the lens body for implantation and positioning within the anterior chamber. After proper positioning, the tool is removed and the stressed clip will spring back through the iridectomy to its nonstressed condition for attaching the lens to the iris.

3 Claims, 9 Drawing Figures

TOOL FOR SURGICAL IMPLANTATION OF AN INTRAOCULAR LENS

BACKGROUND OF THE INVENTION

The present invention relates to ophthalmology, and more particularly to a novel construction of an intraocular lens and a method for surgically implating the intraocular lens in the eye.

Various diseases or conditions of the human eye may require removal of the eye's natural lens. For instance, a serious eye disease, known as a cataract, results in an opaque condition in the lens or its capsule causing partial or total blindness. The opaque condition may be corrected by surgically removing the entire lens or by removing the nucleus material within the capsule. Removal of nucleus material may be accomplished by emulsification of the material and then vacuum withdrawing same. In either case, it has previously been necessary to provide the patient with an exterior contact lens.

However, many post-operative patients, and especially those of advanced age, find it extremely difficult if not impossible to become accustomed to the inconvenience of wearing contact lenses. Accordingly, recent surgical advances have been directed toward implanting artificial intraocular lenses as replacements for removed lenses or lenses in which the nucleus material has been removed. However, there are several significant problems in surgically implanting an intraocular lens. Additionally, it has proved difficult to ensure that the intraocular lens maintains a relatively stable relationship with respect to the iris after implantation.

An example of a prior art intraocular lens is one which includes posterior loops which extend from a rear surface of the lens. Extending outwardly from a peripheral edge of the lens, adjacent one of the loops, is an elongate clip which is deformable for positioning within an adjacent loop. During surgical implantation, the loops are positioned behind the iris in the posterior chamber with the lens being oriented in the anterior chamber. The clip is then manipulated and deformed by the surgeon using a suitable tool so that the clip extends through the iris and is retained by bearing against the loop. The iris is thereby attached to the lens.

Because the clip must be deformed for locking behind the posteriorly positioned loop, it can be appreciated that a continual force will be applied to the loop tending to rotate or twist the loop and possibly the lens in a forward direction. Of course, it may be appreciated that such action could irritate the iris as well as prevent proper optical correction to the patient.

In addition, it must be appreciated that surgical implantation of an intraocular lens is an extremely delicate procedure, involving substantial surgical skill and dexterity. For instance, the overall diameter of the lens body of an intraocular lens may be in the range of five millimeters and the distance between the loops may be in the range of eight millimeters. In order for the surgeon to grip the lens body with forceps and retain any degree of control requires extreme care during insertion of the intraocular lens in the eye. For instance, as the loops are being positioned in the posterior chamber, any inadvertent movement of the surgeon's hand or a repositioning of the forceps may result in the outer surface of the lens body contacting the inner surface or endothelium of the cornea. If such contact occurs, the cornea may become foggy and the implantation of the intraocular lens will not result in achieving satisfactory vision.

Further, it may be appreciated that deforming the clip through the iris to a locking position behind the posterior loop also increases the likelihood that the lens body will shift or twist and contact the endothelium. The important point to be kept in mind in that surgical implantation of an intraocular lens is fraught with difficulties.

Accordingly, it is a general object of the present invention to provide an intraocular lens having a retaining means such as a resilient member formed as a clip which normally assumes a predetermined, nonstressed condition when it is extended into the iris in attaching the iris to the lens body. It is contemplated that the clip must be flexed and elastically deformed to a stressed condition prior to the lens body being positioned in the eye's anterior chamber and then released, whereupon it will return or "spring back" to its nonstressed condition.

Another object of the present invention is to provide a surgical tool adapted for simultaneously holding the lens body and the clip with the clip flexed in its stressed condition. Thus, upon insertion of the lens body in the eye's anterior chamber with the loops being positioned in the posterior chamber, the tool may be removed and the clip will return or "spring back" through an iridectomy (previously provided in the iris) to its nonstressed condition for attaching the iris to the lens body.

Still another object of the present invention is to provide an intraocular lens as described above, which utilizes a clip for locking the iris to the lens body in a nonstressed condition so that no resulting forces are applied on the lens body and consequently to the iris. This substantially stabilizes the lens and prevents it from reorienting in the eye.

These and additional objects and advantages of the present invention will be more clearly understood from a consideration of the drawings and the detailed description of the preferred embodiment.

DETAILED DESCRIPTION OF THE PREFERRED EMBODIMENT

Figure 1:
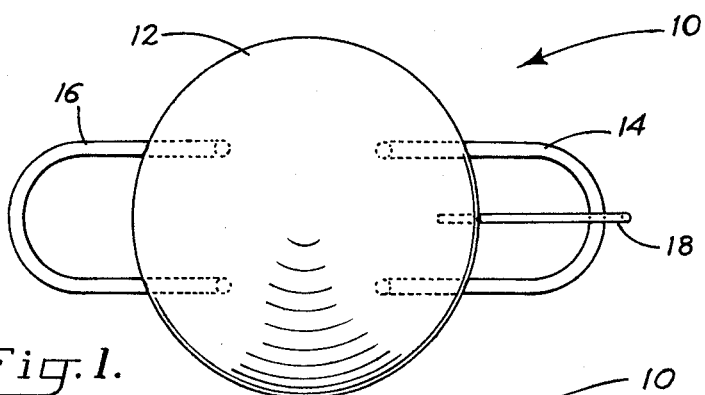
FIG. 1 is a top plan view of a conventional intraocular lens having posterior loops and a clip for locking or attaching the iris to the lens.
Figure 2:
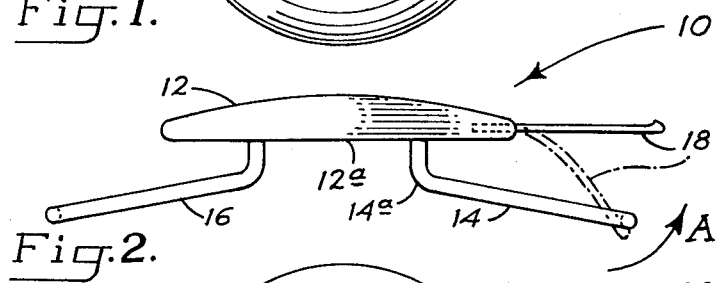
FIG. 2 is a side elevation view of the intraocular lens of FIG. 1.

Turning now to the drawings, and referring to FIGS. 1 and 2, it is deemed necessary to initially describe a conventional intraocular lens which is generally indicated at 10. As can be seen, intraocular lens 10 includes a lens body 12 and a pair of opposed loops 14, 16. The loops are attached to the lens body and extend from a rear surface 12a thereof. The loops are bent as at 14a so that they extend outwardly from the periphery of the lens body.

As can be best seen from a consideration of FIG. 2, a clip 18 is joined to lens body 12 and extends outwardly from a marginal portion thereof. In a conventional implanting procedure using intraocular lens 10, the surgeon grips lens body 12 by means of a lens-holding forceps and positions the posterior loops 14, 16 within the posterior chamber. This orients lens body 12 in the anterior chamber. Next, it is necessary to deform clip 18 so that it extends through an iridectomy previously formed in the iris. More particularly, the surgeon must utilize another tool to force and deform clip 18 through the iridectomy so that is it positioned as shown by the dot-dash outline in FIG. 2. With clip 18 extending through posterior loop 14, it may be appreciated that the clip is biased against the posterior loop and is continuously tending to rotate loop 14 and possibly intraocular lens 10 generally in the direction of arrow A. The resultant rotation may tend to improperly orient the intraocular lens as well as create irritation to the iris or ciliary body.

Additionally, it may also be appreciated that it is extremely difficult for a surgeon to deform clip 18 into its retained or locked position within posterior loop 14 without inadvertently shifting or moving the lens body. As referred to previously, any shifting is to be avoided because contact between the lens body and the endothelium of the cornea may result in a permanently impaired cornea.

Figure 3:
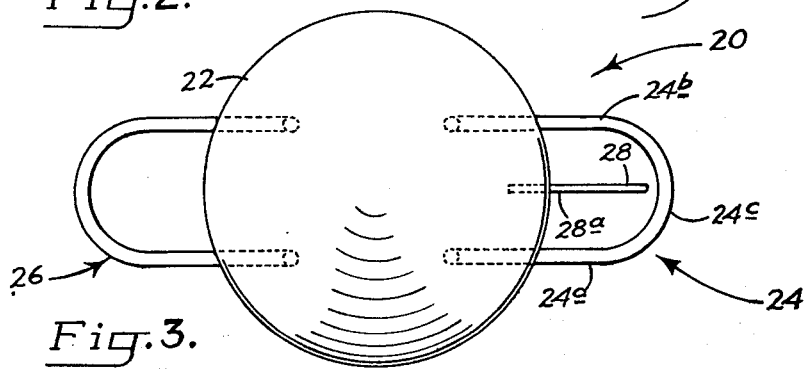
FIG. 3 is a top plan view of an intraocular lens according to the present invention prior to surgical implantation in the eye, a clip being shown in its normally nonstressed condition.
Figure 4:
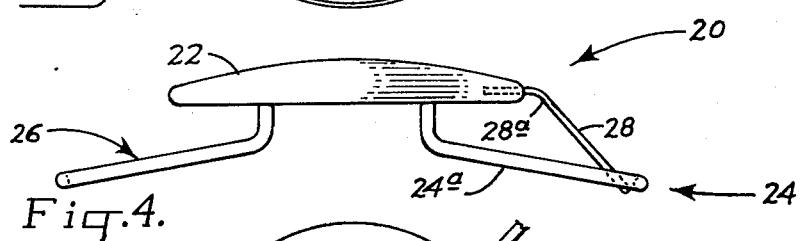
FIG. 4 is a side elevation view of the intraocular lens of FIG. 3.

Turning now to the specific construction of the present invention, attention is directed to FIGS. 3 and 4 which illustrate an improved intraocular lens generally indicated at 20. Intraocular lens 20 includes a conventional lens body 22 and positioning or loop means such as posterior loops 24, 26 which extend from a rear surface of the lens body. Joined to and extending from a peripheral portion of lens body 22 (in cantilever manner) is a retaining means including a resilient member such as elongate clip 28 which is normally directed toward a plane defined by legs 24a, 24b of posterior loop 24. A bend is indicated at 28a intermediate the point of attachment of clip 28 to the lens body and its free end. It is to be noted that clip 28 is dimensioned to freely move through the plane between its stressed and nonstressed conditions in noncontacting manner with posterior loop 24. It must be appreciated that clip 28 assumes the predetermined orientation as illustrated in a nonstressed condition which corresponds to the orientation which will be achieved after the lens is fully implanted in the eye. This will be described in more detail at a later point.

Figure 5:
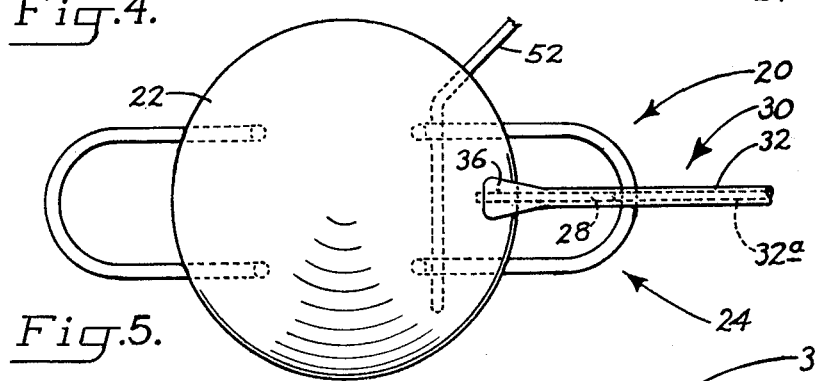
FIG. 5 is a top plan view of the intraocular lens of the present invention illustrating positioning of a detachable tool for holding the lens body and the clip during surgical implantation in the eye.
Figure 6:
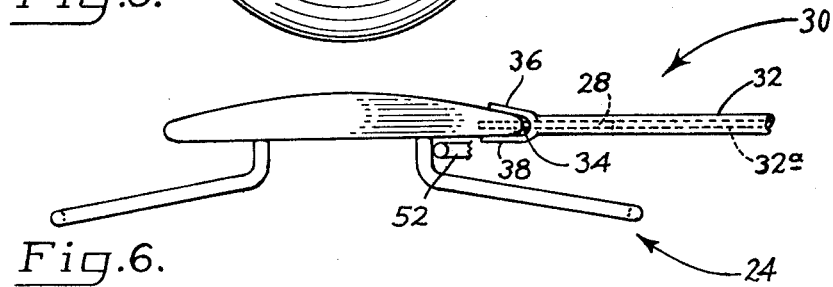
FIG. 6 is a side elevation view of the lens and tool illustrated in FIG. 5.

Turning now to FIGS. 5 and 6, reference is made to a special tool, generally designated at 30, which is used in surgical implantation of intraocular lens 20. Explaining further, it is contemplated that clip 28 will be elastically deformed to a stressed condition and tool 30 will be utilized by the surgeon for simultaneously engaging or holding lens body 22 as well as clip 28. As illustrated, tool 30 includes an elongate means such as member 32 provided with a longitudinal bore 32a extending therethrough. Bore 32a is dimensioned to slideably reveive clip 28 and is also configured to hold lens body 22 when clip 28 is so received. Member 30 is shown with the greater portion of its length cut-away, but it would be dimensioned of a length sufficient for secure gripping by a surgeon.

It may be seen that tool 30 is provided with an open end defining a throat 34 determined by opposed flanges or surfaces 36, 38. With tool 30 receiving clip 28 a predetermined distance within its bore, it can be appreciated that surfaces 36, 38 will frictionally engage opposite sides of the lens body securely. Thus, a surgeon may position intraocular lens 20 by appropriate manipulation of tool 30.

Figure 7:
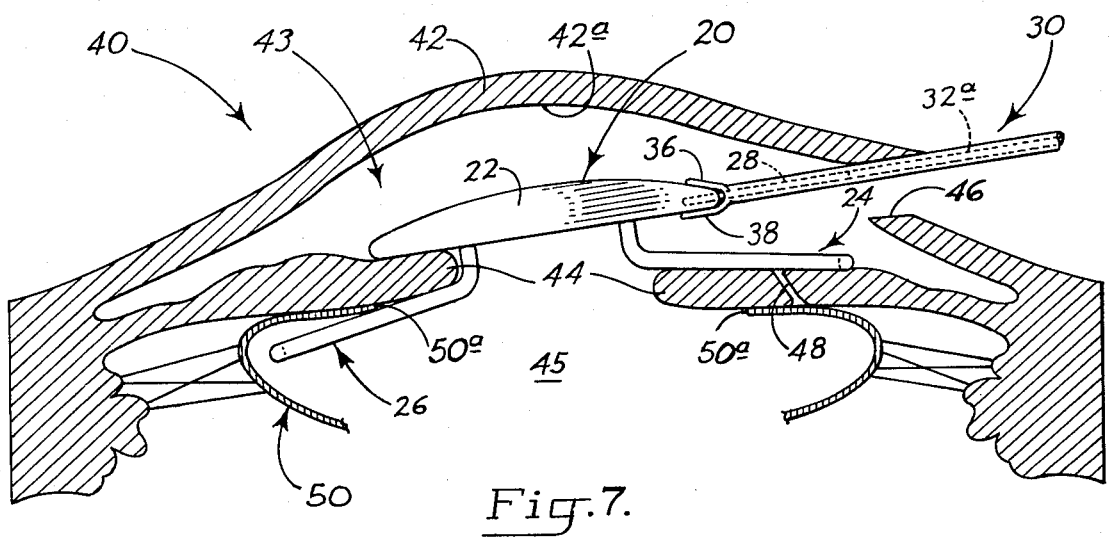
FIG. 7 is a side cross-sectional view, greatly enlarged, taken through a patient's eye (assuming the patient is lying down) illustrating insertion of the intraocular lens of the present invention into the eye.

Generally describing a surgical procedure involving implantation of intraocular lens 20, reference is made initially to FIG. 7. As illustrated, in cross-section, an eye (greatly enlarged) is generally designated at 40 with the cornea being indicated at 42. The inner surface or endothelium of the cornea is indicated at 42a and the anterior chamber at 43. The iris is indicated at 44 and the posterior chamber at 45. A previously made incision is indicated at 46. Another incision or iridectomy is indicated at 48 and is provided in iris 44. The provision of an iridectomy is generally one of surgical preference. The outer membrane or capsule of the eye's natural lens is indicated at 50 and is illustrated with its nucleus removed. The capsule or "bag" has been prepared by the surgeon with an opening, indicated at 50a.

In order to implant intraocular lens 20, the surgeon biases, by means of a suitable tool or instrument, clip 28 so that it is flexed and elastically deformed away from posterior loop 24 a stressed condition. Tool 30 is now positioned so that the free end of clip 28 is inserted in bore 32a and the tool is moved inwardly toward the periphery of lens body 22 until opposed surfaces 36, 38 securely grip the lens body. This is the position shown in FIG. 6. FIG. 7 illustrates initial inserting and positioning of intraocular lens 20 through incision 46. It must be appreciated that the surgeon need not necessarily hold lens body 22 by means of a lens holding forceps. Rather, the surgeon maintains continuous control and stability of the intraocular lens by means of tool 30. As can be seen in FIG. 7, posterior loop 26 has been inserted in posterior chamber 45 within capsule 50 of the "bag."

Figure 8:
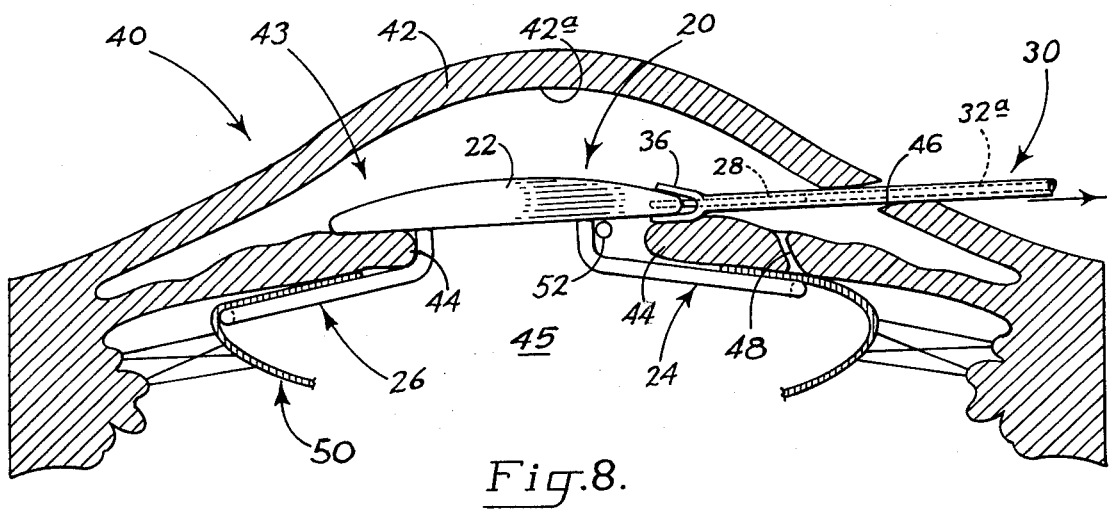
FIG. 8 is a side cross-sectional view, similar to FIG. 7, illustrating positioning of the posterior loops within the posterior chamber prior to positioning of the stabilizing clip through an iridectomy in the iris.
Figure 9:
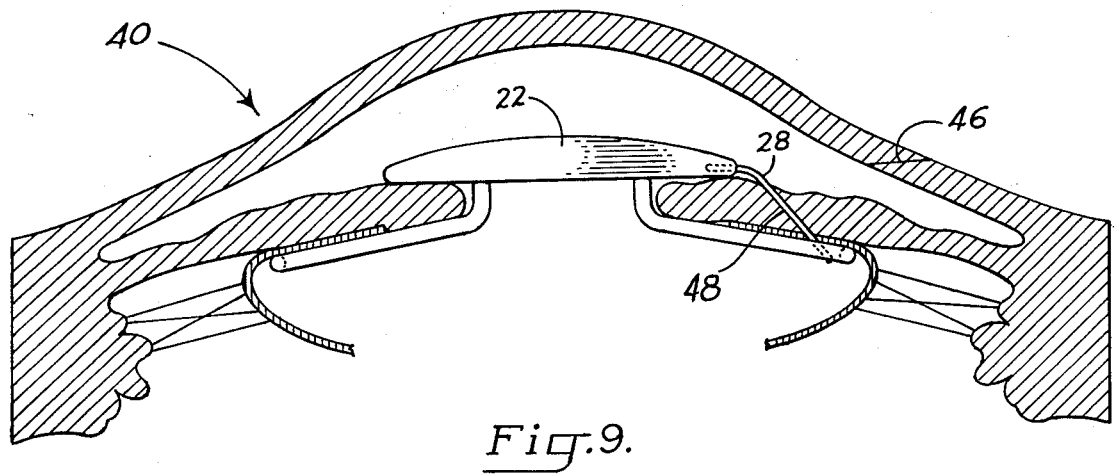
FIG. 9 is a cross-sectional view, similar to FIG. 8, illustrating positioning of the stabilizing clip in its non-stressed condition for locking or attaching the intraocular lens to the iris.

With reference now directed to FIG. 8, it can be seen that additional force is directed against iris 44 (to the left) so that posterior loop 24 may be positioned in posterior chamber 45. This positioning of the posterior loops in the posterior chamber accurately orients lens body 22 in anterior chamber 43 so that iris 44 is sandwiched between the posterior loops and a portion of the rear surface of lens body 22. Clip 28 has been elastically deformed an amount sufficient to provide a gap between the clip and posterior loop 24 to permit reception of a portion of iris 44, as shown. In the position shown in FIG. 8, it is only necessary for the surgeon to release or withdraw tool 30 from engagement with lens body 22 and clip 28 to permit the clip to return to its nonstressed condition. In order to remove tool 30, it may be necessary to position a tool such as a spatula, (an end portion of which is indicated at 52 in FIGS. 5, 6 and 8) against an upright portion of posterior loop 24. Positioning the spatula as indicated permits intraocular lens 20 to be maintained in stable position during removal of tool 30 so that surfaces 36, 38 may be withdrawn from engaging opposed sides of lens body 22. Removal of tool 30 results in releasing clip 28 so that it moves toward posterior loop 24 by "springing back" or returning to its nonstressed condition through iridectomy 48 to thereby securely lock or attach iris 44 to the lens body. It is generally not necessary to provide an iridectomy in capsule 50 adjacent iridectomy 48 because the membraneous material of the capsule is extremely thin and flimsy. With the lens implanted as shown in FIG. 9, spatula 52 is removed, incision 46 is suitably sutured, and the operation is essentially complete.

From the above description, it should be readily apparent that there are several distinct and very important advantages resulting from use of the intraocular lens of the present invention and the method of implanting same. First of all, by providing a clip which normally assumes a nonstressed condition when extending through an iridectomy provided in the iris, (or merely through the iris) it can be seen that no resulting forces are applied to any portion of the lens body. This results in a stabilized locking or attaching of intraocular lens 20 to the iris and prevents resulting forces which may act on the iris tending to rotae the lens body out of position.

Additionally, it may be appreciated that the present invention provides an intraocular lens 20 which may be suitably used with a novel tool 30 for implanting the intraocular lens. With clip 28 flexed to a stressed condition by means of tool 30 simultaneously holdng both lens body 22 and the clip, it is only necessary for the surgeon to grip the tool for placement of the intraocular lens in the capsule or "bag." The surgeon maintains complete control and may "steer" the intraocular lens accurately into position. Upon removal of tool 30, it can be seen that clip 28 will naturally assume the predetermined orientation in a nonstressed condition shown in FIG. 9. It must be emphasized that it is not necessary for the surgeon to grip lens body 22 with a lens-holding forceps in order to effectuate placement. Further, with conventional intraocular lenses, it may be necessary for a surgeon to regrasp the lens body several times with the forceps during urging of a conventional clip through the iridectomy. By regrasping the lens body, the surgeon substantially increases the risk of contact between the lens body and the endothelium. In addition, it can be seen that urging a conventional clip through the iridectomy so that it is locked behind a posterior loop will result in forces being imparted to the lens body which also increases the chances of contact with the endothelium.

In contrast, the present invention of intraocular lens 20 combined with a surgical procedure utilizing tool 30 only requires that the tool be removed from engagement with lens body 22. No regrasping is required and it is not necessary for the surgeon to push or urge clip 28 into its locking position. Rather, clip 28 naturally "springs back" or assumes its nonstressed condition through the iridectomy. The result is much greater simplicity in implanting an intraocular lens with significantly decreased chances for contacting the endothelium.

Of course, another significant advantage of the present invention is that a surgeon knows that removal of tool 30 will absolutely result in clip 28 assuming its predetermined, nonstressed condition in attaching the iris to the lens body. The surgeon always knows the exact position that the clip will assume. Guesswork in deforming or manipulating a clip into its locking position is virtually eliminated.

It should also be apreciated that tool 30 may be designed with a plunger element slideably extending within bore 32a of member 32. The plunger element could be suitably manipulated by the surgeon toward clip 28 for exerting a force thereagainst when it is desired to withdraw tool 30 from engagement with the lens body. Such an arrangement would make it unnecessary to employ spatula 52.

Materials suitable for use in the construction of clip 28 may include polypropylene or platinum-iridium. Of course, other materials may be readily employed as long as the feature of providing the intraocular lens with a clip normally positioned in a nonstressed condition, corresponding to its position extending through the iris, is maintained.

While the invention has been particularly shown and described with reference to the foregoing preferred embodiment, it will be understood by those skilled in the art that other changes in form and detail may be made therein without departing from the spirit and scope of the invention as defined in the appended claims.

It is claimed and desired to secure by Letters Patent:

1. An intraocular lens for surgical implantation in the eye comprising:
   a lens body;
   positioning means extending from said lens body for orienting said lens body in the eye's anterior chamber; and
   retaining means including a resilient member joined to said lens body for extending outwardly from a marginal portion thereof, said resilient member being elastically deformable away from said positioning means to a stressed condition and releasable, when said lens body is implanted, from the stressed condition so that it may move toward said positioning means and assume a predetermined orientation in a nonstressed condition extending into the iris to thereby attach the iris to said lens body.

2. The tool of claim 1 wherein said elongate means includes an end configured to hold the lens body when the retaining means is received a predetermined distance within the bore.

3. The tool of claim 2 wherein said end is defined by a throat having opposed surfaces dimensioned for frictionally engaging opposite surfaces of the lens body to thereby hold same during implantation.

* * * * *